United States Patent [19]
Eldon

[11] Patent Number: 5,578,230
[45] Date of Patent: Nov. 26, 1996

[54] HEATER SYSTEM HAVING HOUSING WITH CHAMBER FOR CREATING A TURBULENT SPINNING AIR VORTEX

[76] Inventor: Richard Eldon, P.O. Box 129, Firestone, Colo. 80520

[21] Appl. No.: 257,269

[22] Filed: Jun. 9, 1994

[51] Int. Cl.$^6$ .............................. A45D 20/10; H05B 1/00
[52] U.S. Cl. ............................................ 219/211; 392/383
[58] Field of Search ................................. 392/379, 380, 392/383, 384, 360, 361, 365, 367, 368, 373; 219/211; 137/808, 810, 811

[56] References Cited

U.S. PATENT DOCUMENTS

| | | | |
|---|---|---|---|
| 2,259,712 | 10/1941 | Sweetland | 392/383 |
| 2,405,783 | 8/1946 | Gardenhour | 392/383 |
| 3,230,556 | 1/1966 | Shippee | 392/383 |
| 3,444,922 | 5/1969 | Dingman | 392/383 |
| 3,989,924 | 11/1976 | Kurtzer | 219/211 |
| 4,042,803 | 8/1977 | Bickford | 219/211 |
| 4,151,658 | 5/1979 | Hibino | 392/383 |
| 4,279,255 | 7/1981 | Hoffman | 219/211 |

*Primary Examiner*—Teresa J. Walberg
*Assistant Examiner*—Sam Paik
*Attorney, Agent, or Firm*—John R. Flanagan

[57] ABSTRACT

A battery operated portable human body heater. The portable heater uses conventional 12 volt batteries to power a portable hot box which provides blowing air with three temperature settings. The portable heater is compact and can be conveniently transported in a carry bag such as a back pack. The heater can be attached to a blanket, a jacket or pants to warm he human body. The heater can be set at high temperature, low temperature or air only. At the high temperature setting continuous 130° F. heat is provided for over an hour. At the low temperature setting continuous 87–100° F. heat is provided for over two hours. Blowing air without heat is provided for over 30 hours. The portable heater can also be powered or its batteries recharged by a typical wall socket or cigarette lighter in a car or boat.

19 Claims, 6 Drawing Sheets

HEATER SYSTEM HAVING HOUSING WITH CHAMBER FOR CREATING A TURBULENT SPINNING AIR VORTEX

FIELD OF THE INVENTION

The present invention relates to a battery operated portable human body heater. This heater is ideally suited for outdoor emergency care, water ski boat drivers and similar applications.

BACKGROUND OF THE INVENTION

Outdoor enthusiasts must often withstand frigid temperatures. Cold weather conditions lead to discomfort and sometimes hypothermia. Solutions to these problems have led to methods of warming the parts of the human body which are most prone to cold and frostbite such as hands and feet. The methods that have been used to accomplish this outdoor warming, range from chemical packs to battery powered socks and mittens. The present invention solves the problem of overall body warming by producing a portable heater system which can be carried in a backpack to warm the entire human body or large portions of it.

In summary, the present invention improves on the prior art by maximizing the usable energy of conventional batteries. The invention surrounds conventional nichrome heating elements with a vortex creating chamber. This increases the heater's output air temperature by 10 to 15% and increases the velocity of the output air by 300%. Output air temperatures of the present invention range from 90 to 133 degrees Fahrenheit for over 90 minutes. An air flow velocity of over 8000 feet per minute is created when the air is piped through a tube with a 1¼ inch inside diameter. This permits effective heating of the upper body via a jacket, the lower body via pants, or the entire body via a woolen blanket. The entire porta-heater weighs under 22 pounds including conventional batteries. The porta-heater, therefore, enables a water ski boat driver to maintain body temperature in high speed chilling winds, or enables an emergency rescuer to carry a 22 pound backpack to a hypothermia victim and render effective first aid warming for up to an hour and a half.

SUMMARY OF THE INVENTION

The main object of the present invention is to provide a portable heater using conventional batteries.

Another object of the present invention is to provide 100° F. output air for over an hour at 8000+feet per minute.

Another object of the present invention is to provide a portable heater using conventional batteries which can be attached to human body closure means such as a jacket, blanket or pants.

Another object of the present invention is to provide a portable heater using conventional batteries which can be conveniently transported using a carrying case.

Another object of the present invention is to surround conventional heating coils with a vortex chamber to increase the temperature and speed of output flow.

Another object of the present invention is to provide baffles in a vortex chamber which surrounds heating coils in order to help create a spinning vortex of air.

Another object of the present invention is to provide a portable heater using conventional batteries in which the temperature can be controlled by a switch.

Another object of the present invention is to provide a portable box using conventional batteries which provides a blowing air supply only.

Another object of the present invention is to provide a portable heater which can be powered by an AC/DC converter from an AC source such as a typical wall socket.

Another object of the present invention is to provide a portable heater with a conventional battery which can be powered by an AC/DC converter from an AC source such as a typical wall socket.

Another object of the present invention is to provide a portable heater with a conventional battery in which the battery can be recharged via and AC/DC converter from an AC source.

Another object of the present invention is to provide a portable heater which can be run off a cigarette lighter in a car or boat via a cigarette lighter jack.

Another object of the present invention is to provide a portable heater in which the conventional battery can be recharged from a cigarette lighter in a boat or car via a cigarette lighter jack.

Other objects of this invention will appear from the following description and appended claims, reference being had to the accompanying drawings forming a part of this specification wherein like reference characters designate corresponding parts in the several views.

PIG. 8 is a graph of the porta-heater air output with a vortex chamber.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

DETAILED DESCRIPTION OF THE PREFERRED EMBODIMENT

Figure 1:
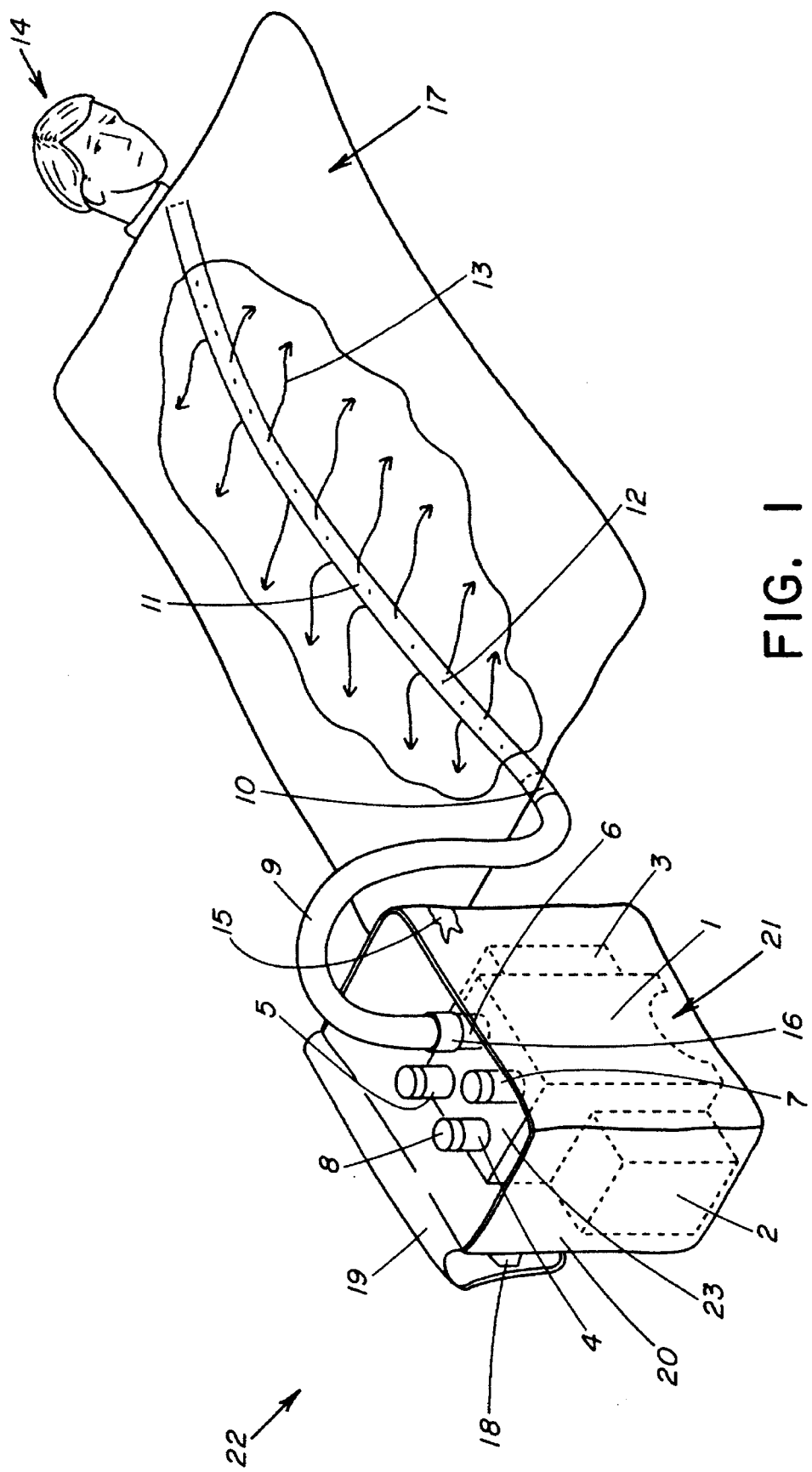
FIG. 1 is a top perspective view of the compact embodiment of the porta-heater and a woolen blanket.

Referring first to FIG. 1 a top perspective view of compact portable heater unit 22 is shown with a hypothermia victim 14. The compact porta-heater 22 is powered by two 12 volt 7 amp hour batteries 2, 3 and is contained in a carry bag 20. The carry bag 20 has a lid 19 which is closed by a hook and loop fastener 15. The compact porta-heater 22 is carried by a handle 18 which is attached to the lid 19 of the carry bag 20.

The compact porta-heater 22 consists of a housing 1 with an air inlet 21 and four air outlets 4–7 attached to its top 23. In the preferred embodiment, the housing 1 has a 7" height and is made of ABS plastic. The top of the housing 23 is a 5" by 5" square. Air intake occurs through ports 21 which are created by a semi-circular cut out with a 1" radius in the bottom half of each side panel of housing 1.

Each air outlet 4–7 is 1" in length, made of an acrylic plastic tube with a 1" I.D. and a 1.25" O.D. Each air outlet 4–7 is closed by a removable lid 8 when not in use. 1¼" I.D. plastic tubing 9 is connected at one end to an outlet 4–7 by a connector 16, and is connected at the other end to perforated tubing 11 by connector 10.. The perforated tubing 11 contains holes 12 which allow the air to flow outward from the tubing as indicated by arrows 13. The hypothermia victim 14 and the perforated tubing 11 are covered by a woolen blanket 17. The woolen blanket 17 traps the warm air 13 against the victim's body.

Figure 2:
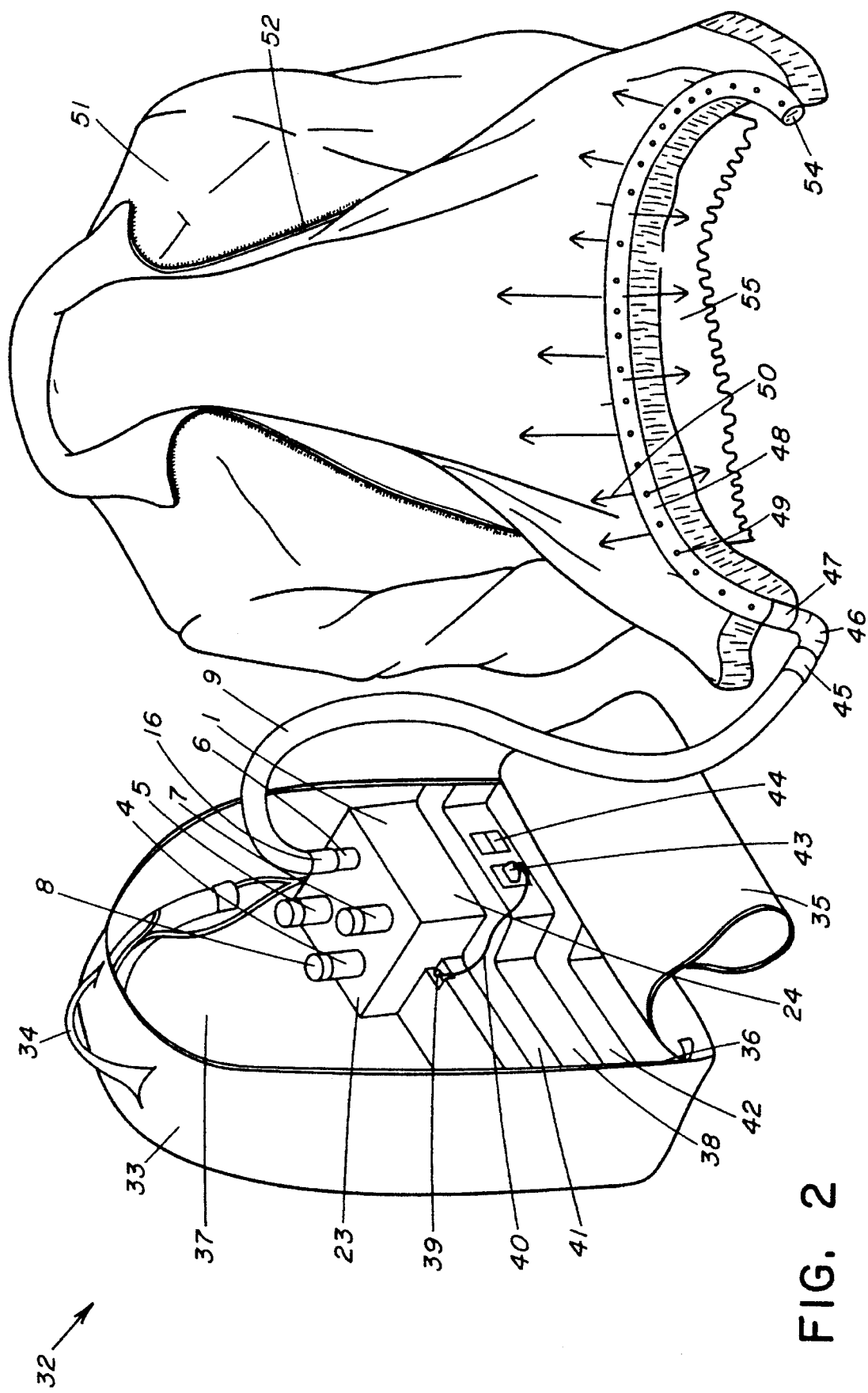
FIG. 2 is a top perspective view of the high power embodiment of the porta-heater with jacket and pants.

Referring next to FIG. 2 a top perspective view of a backpack porta-heater 32 is shown with a jacket 51 and pants 55. The jacket 51 is a light weight nylon windbreaker style and is closed by a zipper 52. The porta-heater 32, its battery 38, and a clothing storage compartment 37 are contained in a backpack 33. The battery 38 and porta-heater housing 1 are held in place by two securing bands 41,42. The backpack 33 has a front panel 35 which is fastened by a zipper 36. The porta-heater 32 is carried by a handle 34 which is attached to the backpack 32.

The backpack porta-heater 32 consists of the same housing 1, housing top 23, outlets 4–7, outlet lids 8, outlet connector 16, and 1¼" I.D. plastic tubing 9 as the embodiment shown in FIG. 1.

The preferred embodiment is a high power porta-heater 32 which is powered by a 12 volt 17 amp hour battery 38. The battery 38 is connected to the porta-heater 32 by a connecting wire 40 which runs from the battery jack 39 to the porta-heater plug 43. The plug 43 is located on the front face 24 of the housing 1 and accepts DC power. The porta-heater power is controlled by the three-way switch 44 and turned off by disconnecting the plug 43 from the power source.

The porta-heater 32 is connected to the jacket 51 and pants 55 by the 1¼" I.D. plastic tubing 9 via a connector 45, a tube joint 46, and a second connector 47. The second connector 47 is attached to the perforated tubing 48 which contains holes 49 and a closure 54 at one end. The holes 49 allow the air to flow outward from the perforated tubing 48, as indicated by arrows 50, filling the jacket 51 and optionally the pants 55 with warm air. The preferred embodiment consists of the jacket 51 because it warms most of the major organs. The pants 55 are optional.

Figure 3:
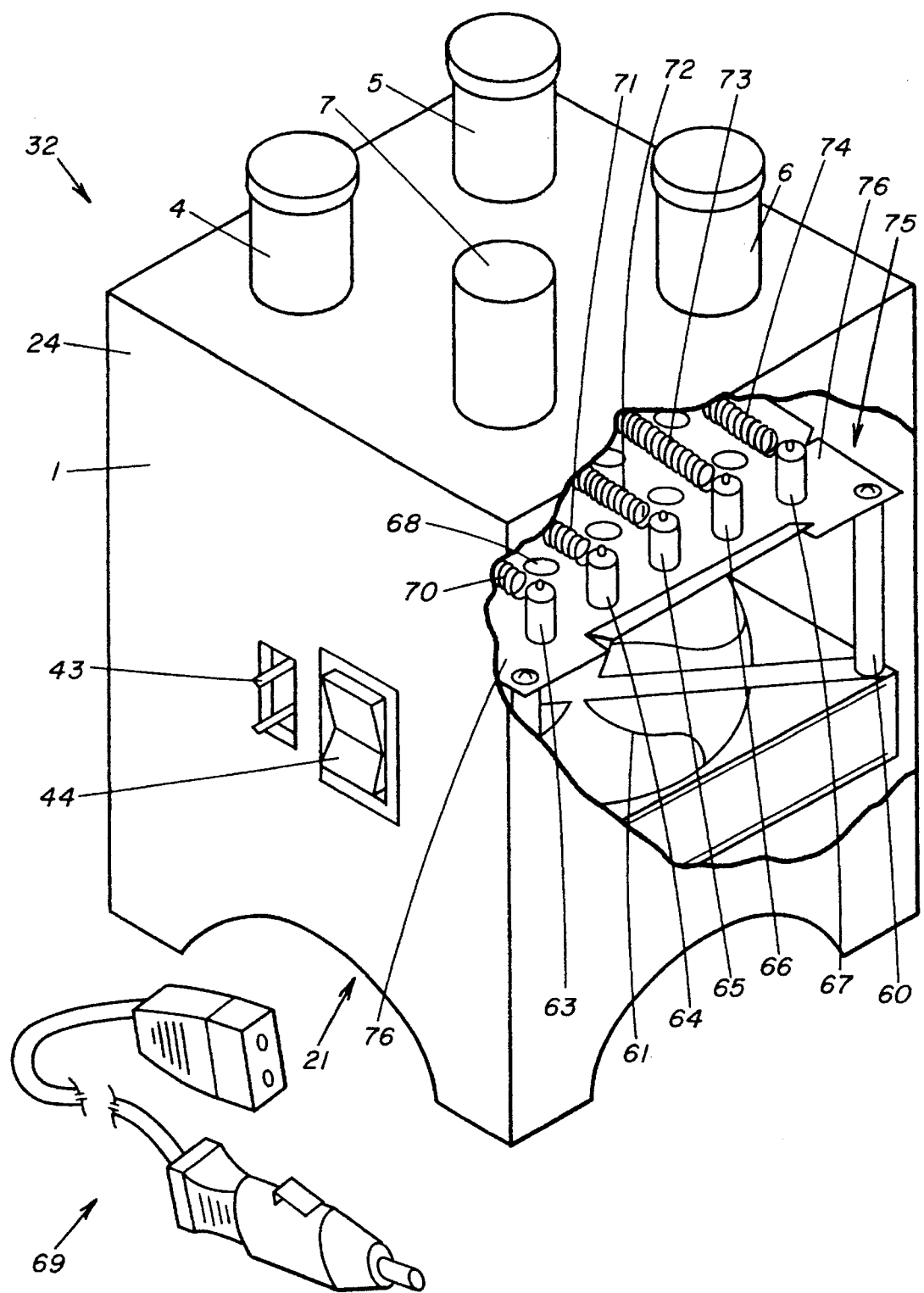
FIG. 3 is a top perspective view of the porta-heater shown in FIG. 2 with a partial cut-away of the left side.

Referring next to FIG.3 a top perspective of the high power porta-heater 32 that was illustrated in FIG. 2 with a partial cut-away of the left side is shown. The housing 1 encloses a fan 61, a vortex chamber 75, and five nichrome heating wires 70–74.

The fan 61 draws air through the air inlet ports 21 and pushes it through 4 rows of 3/16" diameter holes 68 punched into the frame 76. Each row has 5 holes. The frame 76 is supported by a frame member 60. The air is pushed through the holes into the vortex chamber 75 which contains five 0.031 nichrome wires 70–74. The nichrome wires 70–74 are attached to insulator posts 63–67 which are mounted on the frame 76. The nichrome wires are conventional heating elements.

A lighter jack 69 also allows the porta-heater 32 to be powered directly from the cigarette lighter of a boat or car. A cigarette lighter produces 14 volts when the boat or car is running and volts when the car or boat engine is not in operation. The jack 69 is connected at one end to the cigarette lighter and at the other end to the DC accepting plug 43 located on the front face 24 of the housing 1. The jack 69 can also be used to charge the porta-heater battery 38 from the cigarette lighter in a boat or car when the jack 69 is attached to the porta-heater battery 38.

The porta-heater 32 is controlled by a three way switch 44. When the switch is depressed in the high power position all five heating wires 70–74 are in operation. When the switch 44 is depressed in the low position only three heating wires 70, 72, and 74 are in operation. When the switch 44 is not depressed but is in the middle position, air flow is provided but no heating wires are in operation. The porta-heater 32 is turned off by disconnecting the plug 43 from the energy source.

A 17 amp hour battery will power the porta-heater 32 for 1.6 hours at the high power setting, for 2.9 hours at the low power setting, and for 34 hours at the air only setting. These numbers are based on Ohm's law which is as follows:
E=IR, where E is voltage, I is current and R is resistance.
P=EI=$E^2$, where P is power.
Capacity=17 amp hours=I(time).

The following table shows the air flow speed and temperature that can be maintained in the preferred high power embodiment of the porta-heater 32 when varying numbers of outlets 4–7 are in use.

| At the air only setting: # of outlets in use: | Air speed in feet/minute: | |
|---|---|---|
| 4 outlets | 1100 FPM | |
| 3 outlets | 1300 FPM | |
| 2 outlets | 1450 FPM | |
| 1 outlet | 1550 FPM | |
| At the low temperature setting: # of outlets in use: | Air flow speed in feet/minute: | Temperature in degrees Fahrenheit provided for 2.9 hours: |
| 4 outlets | 700 FPM | 94 |
| 3 outlets | 1000 FPM | 87 |
| 2 outlets | 1150 FPM | 96 |
| 1 outlet | 1250 FPM | 102 |
| At the high temperature setting: # of outlets in use: | Air speed in feet/minute: | Temperature in degrees Fahrenheit provided for 1.6 hours: |
| 4 outlets | 600 FPM | 96 |
| 3 outlets | 950 FPM | 102 |
| 2 outlets | 1100 FPM | 110 |
| 1 outlet | 1200 FPM | 135 |

Figure 4:
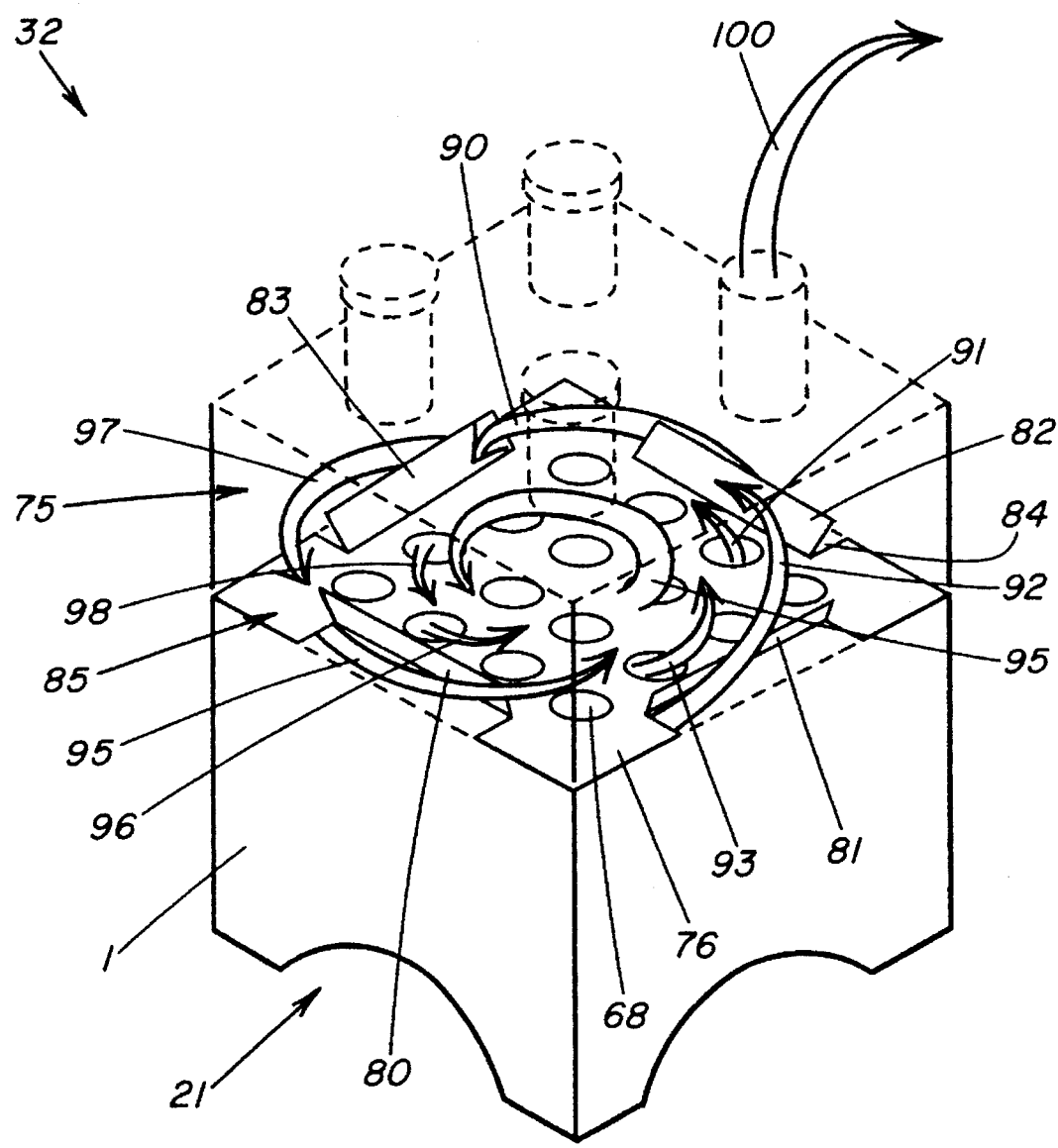
FIG. 4 is a top perspective view of the vortex chamber of the porta-heater shown in FIGS. 2, 3.

Referring next to FIG. 4 a top perspective view of the vortex chamber 75 that was illustrated in FIG. 3 is shown. The housing 1 of the high power porta-heater 32 encloses a vortex chamber 75. The floor of the vortex chamber is created by the frame 76. Each of the four edges of the frame are slit and bent upward at an acute angle 84 to form four baffles 80–84. The baffles serve to help create the spinning air vortex 85.

The porta heater 32 takes up air through the air inlet which is the same as that shown in FIG. 1. The fan 61 pushes the air through the holes 68 and into the vortex chamber 75 which creates a vortex 85. The vortex is made of input air current elements as indicated by arrows 90–98. The air is ultimately forced out of one or more of the outlets 4–7 as output airflow indicated by the arrow 100. The vortex chamber 75 greatly increases the heat transfer efficiency and the speed of the output airflow of the porta-heater 32.

Figure 5:
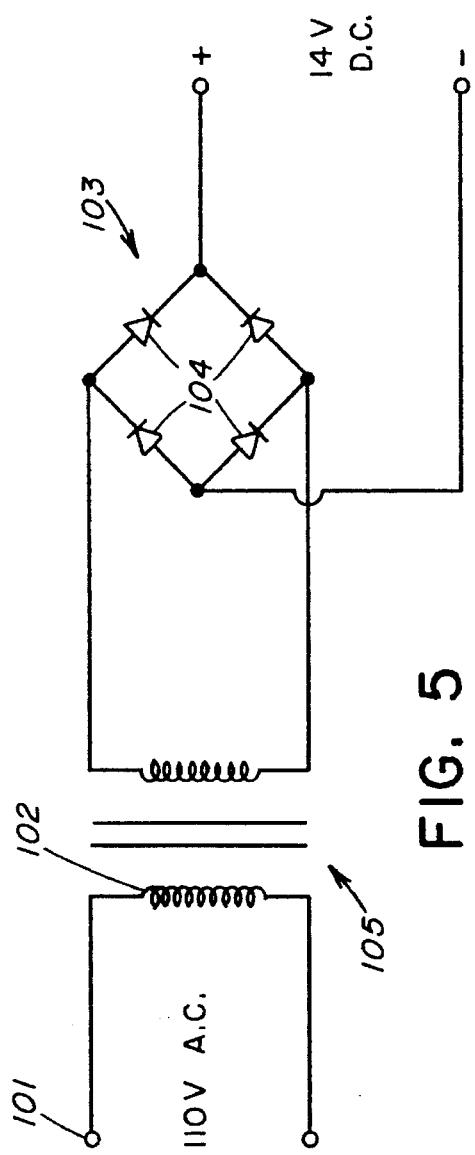
FIG. 5 is an electronic schematic of the AC/DC converter.

Referring next to FIG. 5 an electronic schematic of a conventional AC to DC converter 105 that is well known in the art is shown. The converter 105 consists of a power input element 101, a transformer 102, and a bridge rectifier 103 which consists of four diodes 104. The converter 105 allows the ports-heater 32 to be powered directly from a 110 volt AC source such as a typical wall socket. The converter 105 can also be used to recharge the battery 38 when the converter 105 is attached to the porta-heater battery 38.

Figure 6:
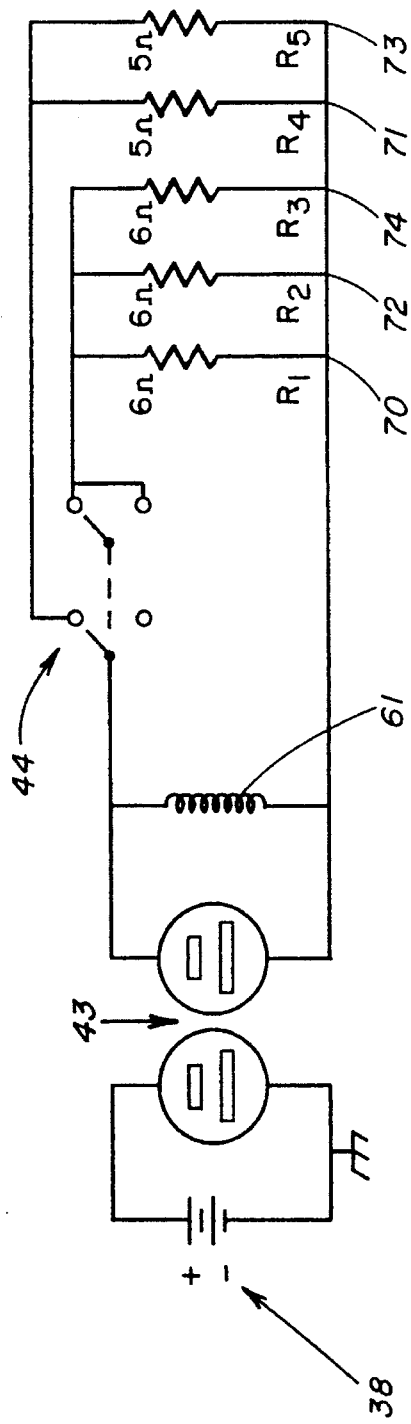
FIG. 6 is an electronic schematic of the heating system.

Referring next to FIG. 6 an electronic schematic of the porta-heater 32 is shown. The porta-heater 32 consists of a battery 38 which is connected to a polarized plug 43, a fan 61, a double pole double throw switch 44 and five resistors 70–74 that are wired in parallel. Three 6 ohm resistors 70, 72, and 74 are in operation when the porta-heater 32 is switched to the low temperature setting. All five resistors 70–74, including two 5 ohm resistors 71, 73, are in operation when the porta-heater 32 is switched to the high temperature setting by switch 44.

Figure 7:
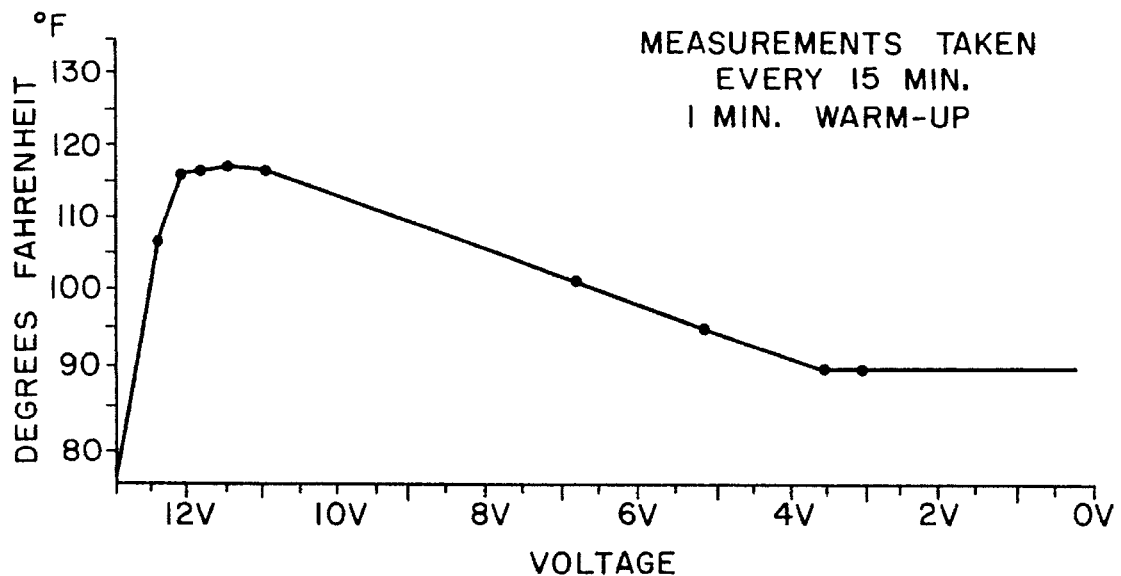
FIG. 7 is a graph of the porta-heater air output without a vortex chamber.

Referring next to FIG. 7 a graph of the porta-heater 32 air output without a vortex chamber is shown. The following table presents the data points that are plotted in FIG. 7:

| Time in minutes | Volts | Amps | Temp. in °Farenheit | Velocity in feet per minute |
| --- | --- | --- | --- | --- |
| Start | 12.47 | 11+ | 107 | 3100 |
| 15 | 12.03 | 10.50 | 116 | 3100 |
| 30 | 11.81 | 10.25 | 116 | 3100 |
| 45 | 11.52 | 10.00 | 117 | 2700 |
| 60 | 10.93 | 9.60 | 116 | 2700 |
| 75 | 6.78 | 5.90 | 102 | 900 |
| 90 | 5.27 | 4.50 | 95 | 900 |
| 105 | 3.57 | 2.95 | 90 | 400 |
| 109 | 3.30 | 2.60 | 90 | dead |

Figure 8:
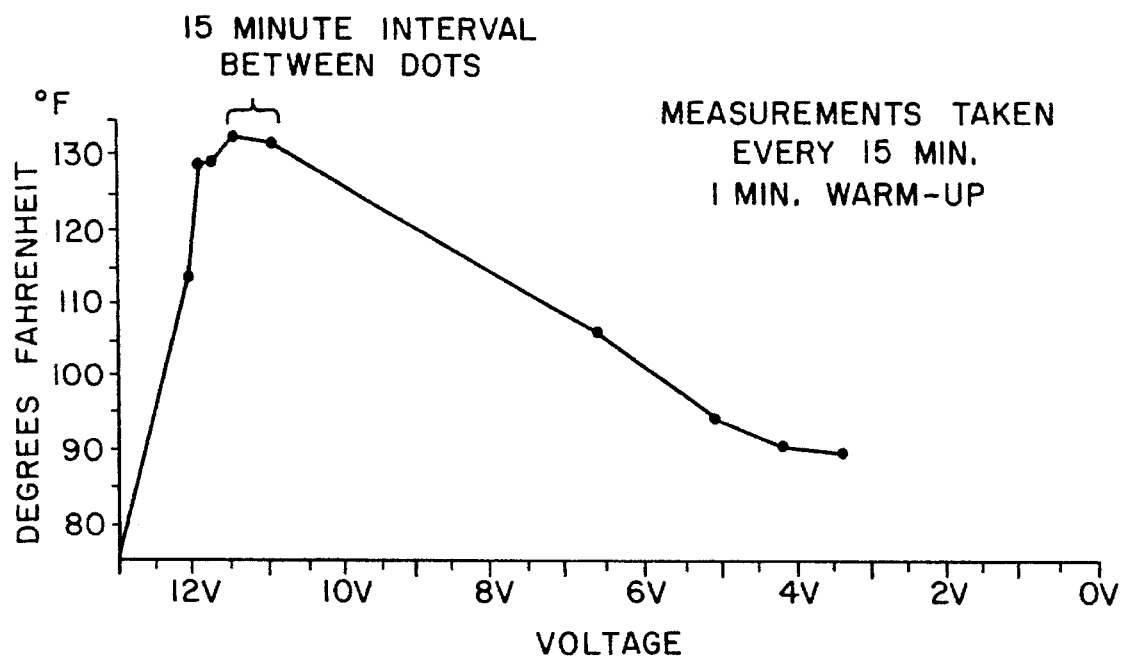

Referring next to FIG. 8 a graph of the porta-heater 32 air output with a vortex chamber is shown. The following table presents the data points that are plotted in FIG.8:

| Time in minutes | Volts | Amps | Temp. in °Farenheit | Velocity feet per min. |
| --- | --- | --- | --- | --- |
| start | 12.26 | 10.5 | 114 | 10,000+ |
| 15 | 12.02 | 10.5 | 128 | 10,000+ |
| 30 | 11.81 | 10.2 | 128 | 10,000+ |
| 45 | 11.55 | 10.0 | 133 | 8,000 |
| 60 | 11.06 | 9.6 | 132 | 8,000 |
| 75 | 6.69 | 5.7 | 107 | 1100 |
| 90 | 5.21 | 4.3 | 95 | 1100 |
| 105 | 4.39 | 3.5 | 91 | 600 |
| 111 | 3.41 | 2.8 | 91 | dead |

FIG. 7 and FIG. 8 show that a vortex chamber increases the temperature and speed of the porta-heater's 32 output air flow. The vortex chamber increases the efficiency of the heat transfer between the heating wires 70–74 and the input air current elements 90–98 by creating turbulent rather than laminar air flow. With turbulent air flow more molecules collide with the heating wires 70–74, thereby increasing the efficiency of heat transfer.

The vortex chamber 75 maintains a pressure head on a dynamic column of air when the air flow is forced through the vortex chamber 75 of FIG. 4. This pressure head is sustained all the way to the jacket 51 of FIG. 2 causing the jacket to retain the warm air in intimate contact with the human body. Without the pressure head, the warm air would not be held in the jacket 51 but would quickly leak out.

Although the present invention has been described with reference to preferred embodiments, numerous modifications and variations can be made and still the result will come within the scope of the invention. No limitation with respect to the specific embodiments disclosed herein is intended or should be inferred.

I claim:

1. A heating system, comprising:

a source of electrical power;

a housing having an air inlet means, an air outlet means spaced from said air inlet means, and a vortex chamber formed between said air inlet means and said air outlet means;

a heating element disposed in said vortex chamber of said housing adjacent to said air outlet means and being operable upon connection to said source of electrical power to produce heating of air in said vortex chamber of said housing;

a fan disposed adjacent to said vortex chamber of said housing and adjacent to said air inlet means and being operable upon connection to said source of electrical power to produce a flow of air through said vortex chamber of said housing past said heating element from said air inlet means to said air outlet means of said housing; and vortex generating means defined in said vortex chamber of said housing adjacent to said heating element for forcing said flow of air produced by said fan into a turbulent spinning air vortex in said vortex chamber in contact with said heating element so as to increase air temperature and speed of air flow exiting said housing with said vortex generating means present in said vortex chamber over the temperature and speed of a laminar air flow which would exit said housing without said vortex generating means present in said vortex chamber; and said vortex generating means comprises a frame disposed in said housing and extending across said vortex chamber, said frame having a plurality of holes therein;

said heating element being attached to said frame and disposed between said frame and said air outlet means; and said fan being disposed between said frame and said air inlet means and being operable to push said airflow through said holes in said frame and into close proximity to said heating element.

2. The heating system of claim 1, wherein:

said air outlet means further comprises an output tube connected to said air outlet means; and said system further comprises a perforated tube extending from said output tube.

3. The heating system of claim 2, further comprising:

a body closure means for encompassing said perforated tube.

4. The heating system of claim 3, wherein:

said body closure means further comprises a blanket.

5. The heating system of claim 3, wherein:

said body closure means further comprises a jacket; and said jacket further comprises a closure means.

6. The heating system of claim 3, wherein:

said body closure means further comprises pants.

7. The heating system of claim 1, wherein:

said heating element comprises a plurality of heating coils and switch means connected between said heating coils and said source of electrical power for selectively activating said heating coils.

8. The heating system of claim 1, wherein:

said air outlet means of said housing further comprises a plurality of outlet means having closure means functioning to prevent airflow when said outlet means are not in use.

9. The heating system of claim 1, wherein:

said frame further has a plurality of outer edges;

said outer edges each further forming a baffle means bent upward at an acute angle and functioning to help create said turbulent spinning air vortex.

10. The heating system of claim 1, further comprising:

a body closure means attached to said air outlet means.

11. The heating system of claim 10, wherein:

said power source is one high capacity battery; and said housing, said battery, and said body closure means are containable in a carrying case.

12. The heating system of claim 10, wherein:

said power source further comprises two compact lighter weight batteries; and said housing, said batteries, and said body closure means are containable in a carrying case.

13. The heating system of claim 10, wherein:

said power source is a cigarette lighter; and said housing is connected to said cigarette lighter by a cigarette lighter jack.

14. The heating system of claim 10, wherein:

said vortex generating means comprises a frame disposed in said housing and extending across said vortex chamber, said frame having a plurality of holes and baffles formed therein;

said heating element is attached to said frame and disposed between said frame and said air outlet means; and said fan is disposed between said frame and said air inlet means and being operable to push said airflow through said holes and baffles in said frame and into close proximity to said heating coil.

15. The heating system of claim 14, wherein:

said heating element comprises a plurality of heating coils and switch means connected to said heating coils and operable to selectively activate said heating coils so as to adjust the temperature of said vortex chamber to at least three different levels.

16. The heating system of claim 1, wherein:

said power source is an electrical current from an AC source.

17. The heating system of claim 1, further comprising:

a carrying case for holding said housing and said source of electrical power.

18. The heating system of claim 17, wherein:

said carrying case is a backpack;

said backpack having a handle means and closure means.

19. The heating system of claim 1, wherein:

said vortex generating means comprises a frame disposed in said housing and extending across said vortex chamber, said frame having a plurality of baffles extending along outer edges of said frame and each being bent at an acute angle relative to said frame so as to help create said turbulent spinning air vortex in said vortex chamber of said housing;

said heating element is attached to said frame and disposed between said frame and said air outlet means and contacting said turbulent spinning air vortex; and said fan is disposed between said frame and said air inlet means and being operable to push said airflow through said frame adjacent to said baffles and into close proximity to said heating element.

* * * * *